(12) United States Patent
Matsuda et al.

(10) Patent No.: US 7,662,891 B2
(45) Date of Patent: Feb. 16, 2010

(54) AMINE SALT COMPOUND OF CARBOXYLIC ACID HAVING THERMAL DISSOCIATION PORTION AND COMPOUNDING AGENT FOR RUBBER VULCANIZATION AND RUBBER COMPOSITION CONTAINING THE SAME

(75) Inventors: Takashi Matsuda, Hiratsuka (JP); Wonmun Choi, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 229 days.

(21) Appl. No.: 11/956,011

(22) Filed: Dec. 13, 2007

(65) Prior Publication Data

US 2008/0146746 A1 Jun. 19, 2008

(30) Foreign Application Priority Data

Dec. 14, 2006 (JP) ............................. 2006-336747

(51) Int. Cl.
*C08F 8/34* (2006.01)
*C08C 19/20* (2006.01)
*C08J 3/24* (2006.01)
*C07D 207/36* (2006.01)

(52) U.S. Cl. ............... 525/332.7; 525/332.6; 525/348; 525/351; 525/375; 525/378; 548/544; 548/545; 548/547; 568/41; 568/44; 568/45; 568/54

(58) Field of Classification Search ........... 525/332.6, 525/332.7, 348, 351, 375, 378; 548/544, 548/545, 547; 568/41, 44, 45, 54
See application file for complete search history.

(56) References Cited

U.S. PATENT DOCUMENTS

2007/0082984 A1* 4/2007 Choi .................... 524/105

FOREIGN PATENT DOCUMENTS

| JP | 06-271713 | 9/1994 |
|---|---|---|
| JP | 2002-088015 | 3/2002 |
| JP | 2003-138085 | 5/2003 |
| JP | 2004-277705 A | 10/2004 |
| JP | 2007-106677 A | 4/2007 |

OTHER PUBLICATIONS

Office Action issued by the Japanese Patent Office in related Japanese Application No. 2006-336747 on Apr. 8, 2008.

* cited by examiner

*Primary Examiner*—Roberto Rábago
(74) *Attorney, Agent, or Firm*—Connolly Bove Lodge & Hutz LLP

(57) ABSTRACT

To provide a compound which has a higher vulcanization efficiency and superior heat aging resistance compared to conventional compounding agents for rubber compositions and which is environmentally friendly.

An amine salt compound of a carboxylic acid containing a thermal dissociation portion having the Formula (I):

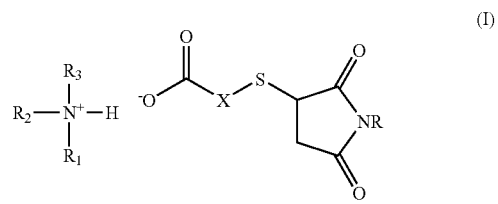

wherein R represents an organic group selected from a $C_1$ to $C_{20}$ alkyl group, a $C_3$ to $C_{10}$ cycloalkyl group, a $C_6$ to $C_{20}$ aryl group and a $C_7$ to $C_{30}$ alkaryl group, $R_1$, $R_2$ and $R_3$ independently represent a hydrogen atom or a $C_1$ to $C_{20}$ organic group which may have a heteroatom and/or a substituent group and X represents a $C_2$ to $C_{20}$ organic group which may have a heteroatom and/or a substituent group and a compounding agent for rubber vulcanization and a rubber composition containing the same.

4 Claims, No Drawings

AMINE SALT COMPOUND OF CARBOXYLIC ACID HAVING THERMAL DISSOCIATION PORTION AND COMPOUNDING AGENT FOR RUBBER VULCANIZATION AND RUBBER COMPOSITION CONTAINING THE SAME

RELATED APPLICATIONS

This application claims priority to Japanese Application No. 2006-336747 filed Dec. 14, 2006, disclosure of which is incorporated herein by reference.

TECHNICAL FIELD

The present invention relates to an amine salt compound of a carboxylic acid containing a thermal dissociation portion and a compounding agent for rubber vulcanization and a rubber composition containing the same. More specifically, it relates to an amine salt compound of a carboxylic acid containing a thermal dissociation portion having a high vulcanization efficiency, having a superior resistance to aging and furthermore is environmentally friendly.

BACKGROUND ART

Generally, when diene-based rubbers are cross-linked with sulfur, it is known in the art that the cross-linked bonds are mainly comprised of polysulfide bonds which easily disassociate under heating and, therefore, are inferior in heat aging resistance. On the other hand, butyl rubbers have superior heat aging resistance, compared with diene-based rubbers, but have the problems of smaller reactive portions capable of being utilized for the vulcanization reaction and, therefore, a slow vulcanization reaction compared with diene-based rubbers and difficulty in co-vulcanization with the other diene-based rubbers. In view of these problems, as a vulcanization agent or co-vulcanization agent, a compound of a thiol/maleimide adduct having active hydrogen-containing groups and which, upon heating, releases a maleimide compound and generates thiol groups has already been proposed (see Japanese Patent Publication (A) No. 2004-277705). The compound set forth in this patent publication, when used as a vulcanization agent or covulcanization agent of butyl rubber, gives an unvulcanized rubber exhibiting a high storage stability and a rubber obtained by vulcanization exhibiting a high thermal stability. However, it is still necessary to prevent or delay the scorching of the unvulcanized rubber composition and to improve the tensile characteristics and the heat aging resistance of the vulcanized rubber. Therefore, the present inventors found a compound which is capable of preventing or delaying the scorching of an unvulcanized rubber composition and of improving the tensile characteristics and heat aging resistance of the vulcanized rubber, that is, an N-substituted succinimide thio group-containing carboxylic acid metal salt, which was previously filed as a Japanese Patent Application No. 2005-296241.

SUMMARY OF THE INVENTION

Accordingly, an object of the present invention is to provide a compounding agent for rubber vulcanization which can be used in a rubber formulation not using zinc oxide, is environmentally friendly, has a higher vulcanization efficiency and is superior in the heat aging resistance compared with conventional rubber compounding agents and exhibits a performance better them that of conventional products.

In accordance with to the present invention, there is provided an amine salt compound of a carboxylic acid containing a thermal dissociation portion having the formula (I):

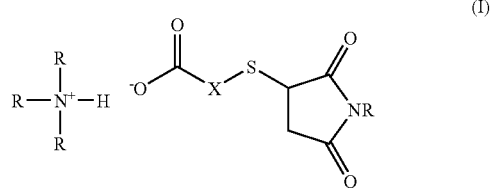

wherein R represents an organic group selected from the group consisting of $C_1$ to $C_{20}$ alkyl groups, $C_3$ to $C_{10}$ cycloalkyl groups, $C_6$ to $C_{20}$ aryl groups and $C_7$ to $C_{30}$ alkaryl groups, $R_1$, $R_2$ and $R_3$ independently represent a hydrogen atom or a $C_1$ to $C_{20}$ organic group which may have a heteroatom and/or a substituent group and X represents a $C_2$ to $C_{20}$ organic group which may have a heteroatom and/or a substituent group and a compounding agent for rubber vulcanization and a rubber composition containing the same.

According to the present invention, the inventors found the novel compound having the above formula (I) and its synthesis method and found that, when this compound is used in combination with a halogen-based rubber provides a higher vulcanization efficiency and superior heat aging resistance over conventional compounding agents and provides a performance equal to or greater than in the past even without adding zinc oxide.

BEST MODE FOR CARRYING OUT THE INVENTION

According to the present invention, the amine salt of a carboxylic acid having the formula (I) containing a thermal dissociation portion in one molecule can be produced by reacting a carboxylic acid (II) and an amine (III) as shown by the following reaction scheme:

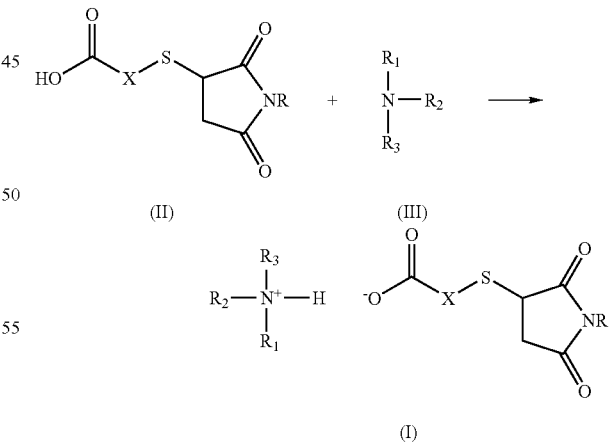

wherein R is an organic group selected from the group consisting of $C_1$ to $C_{20}$ alkyl groups, $C_3$ to $C_{10}$ cycloalkyl groups, $C_6$ to $C_{20}$ aryl groups and $C_7$ to $C_{30}$ alkaryl groups; X is a $C_1$ to $C_{20}$ organic group selected from the group consisting of alkylene groups, cycloalkylene groups, arylene groups, alkarylene groups, and heterocyclic groups, and, as the heteroatom of X, for example, S, N and O may be mentioned, and, as a substituted group, for example, a halogen atom, alkyl group, and alkoxy group may be mentioned, and $R_1$, $R_2$ and $R_3$ are independently a hydrogen or a $C_1$ to $C_{20}$ heteroatom and/or a substituent group.

The above reaction reacts a carboxylic acid (II) having a thermal dissociation portion (e.g., N-substituted succinimide thio group) in the molecule thereof and an amine (III) in a suitable solvent (e.g., water, alcohol such as methanol, ethanol, propanol, and ethylene glycol, acetone, methylethylketone, N-methyl-2-pyrrolidone, tetrahydrofuran, N,N-dimethylformamide, toluene, xylene, pentanehexane) at a temperature 0° C. to 130° C., whereby an amine salt compound of a carboxylic acid having the formula (I) can be produced.

Regarding the organic groups of R, $R_1$, $R_2$ and $R_3$, as specific examples of the alkyl groups among such organic groups, for example, a methyl group, ethyl group, n-propyl group, isopropyl group, n-butyl group, isobutyl group, sec-butyl group, tert-butyl group, hexyl group, n-octyl group, n-dodecyl group, stearyl group, etc. may be mentioned. As specific examples of the cycloalkyl group, for example, a cyclohexyl group etc. may be mentioned. As specific examples of the aryl group, for example, a phenyl group, naphthyl group, etc. may be mentioned. As a specific example of the alkaryl group, for example, a benzyl group, phenyl ethyl group, phenyl propyl group, etc. may be mentioned. With respect to the organic group X, as specific examples of the alkylene group, for example, a methylene group, ethylene group, propylene group, butylene group, hexylene group, octylene group, etc. may be mentioned. As specific examples of the cycloalkylene group, for example, a cyclohexylene group may be mentioned. As a specific example of an arylene group, for example, a 1,2-phenylene group, 1,3-phenylene group, 1,4-phenylene group, biphenyl-4,4'-dyl group, diphenyl methan-4,4'-diyl group, 3,3'-dimethyl biphenyl-4,4'-diyl group, etc. may be mentioned, as specific examples of the alkarylene group, for example, an o-xylylene group, m-xylylene group, p-xylylene group, etc. may be mentioned, as specific examples of the heterocyclic group, for example, a 1,3,4-thiadiazole group, tetrazole group, pyridilene group, 1,3,5-triazine group, etc. may be mentioned. As specific examples of the substituent groups which may be further present in the group X, for example, a methoxy group, ethoxy group, chloro group, bromo group, hydroxy group, etc. may be mentioned.

The amine salt compound of a carboxylic acid containing a thermal dissociation portion having the formula (I) according to the present invention is useful as a compounding agent for rubber vulcanization, specifically as a cross-linking agent, vulcanization accelerator and an acid acceptor.

The rubber composition according to the present invention can be obtained by blending, into 100 parts by weight of an unvulcanized rubber component selected from the group consisting of diene-based rubbers and halogenated rubbers, 0.5 to 10 parts by weight, desirably 0.5 to 5.0 parts by weight, of an amine salt compound of a carboxylic acid containing a thermal dissociation portion having the formula (I). If the amount of the amine salt compound of a carboxylic acid having the formula (I) is small, the cross-linking efficiency deteriorates and the vulcanization rate becomes slower, and, therefore, this is not desirable, while conversely if it is great, scorching becomes easier, and, therefore, this is not desirable.

As the diene-based rubbers usable in the present invention, for example, isoprene copolymer rubber, natural rubber, butadiene rubber, styrene-butadiene copolymer rubber, chloroprene rubber, ethylene-propylene diene copolymer rubber, acrylonitrile-butadiene copolymer rubber and the like may be used. As halogenated rubbers, for example, brominated butyl rubber, chlorinated butyl rubber and other halogenated butyl rubber, isobutylene-para-methyl styrenen copolymer halides (e.g., bromides), chloroprene rubber, epichlorohydrin rubber, chlorosulfonated polyethylene, chlorinated polyethylene, maleic acid-modified chlorinated polyethylene, chlorinated acrylic rubber, fluororubber, epoxylated acrylic rubber, an acrylic rubber obtained from the copolymerization of a halogen-based monomers, etc. may be mentioned. These rubbers can be used alone or in any mixtures thereof.

As specific examples of an amine salt compound of a carboxylic acid having the formula (I) according to the present invention, for example, the following compounds may be mentioned.

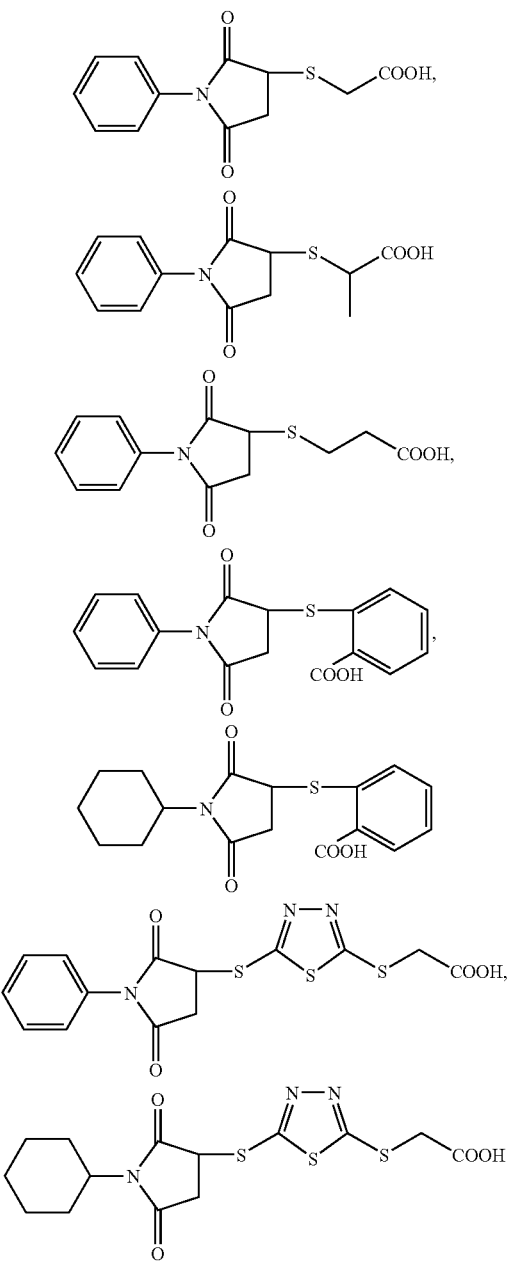

-continued

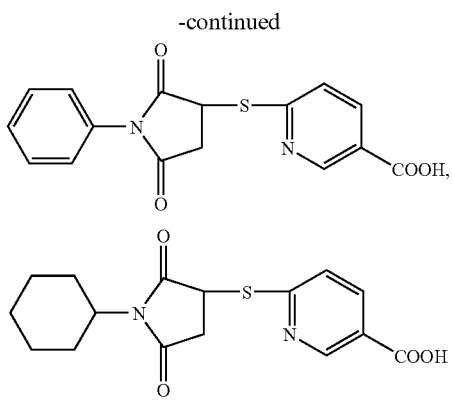

In the rubber composition according to the present invention, in addition to the above components, it is possible to compound carbon black and silica and other (reinforcing agents), vulcanization or cross-linking agents, vulcanization or cross-linking accelerators, various oils, anti-oxidants, plasticizers, and other various additives which are generally used for tire and other rubber composition. Such additives are mixed by a general method, for example, by a roll, Banbury mixer, kneader or the like to form compositions for use for vulcanization or cross-linking. The amounts of these additives may be made the conventional generally used amounts so long as they do not adversely affect the object of the present invention.

EXAMPLES

Examples will now be illustrated to further explain the present invention, but the scope of the present invention is by no means limited to these Examples.

Preparation Example 1

Synthesis of Compound 1

To 150 ml of methanol, 80 g (0.245 mol) of an N-substituted succinimide thio group-containing carboxylic acid and 27.9 ml (0.245 mol) of cyclohexyl amine were charged and the mixture was reacted at room temperature for 10 minutes. After the end of the reaction, the methanol was removed under a reduced pressure and the resultant mixture was filtered. The product was washed with acetone twice and dried, then was subjected to the reaction of the following formula to thereby obtain a white powder compound 1 in an amount of 103 g (yield 99%):

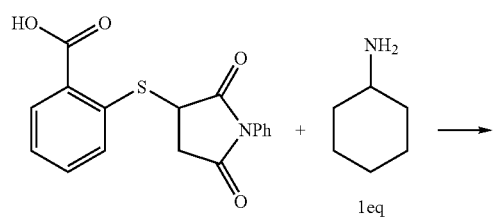

-continued

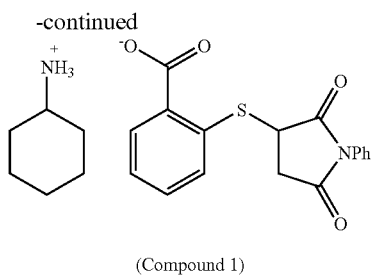

(Compound 1)

$^1$N NMR (400 MHz, DMSO-d6) δ in ppm: 1.0-1.3, 1.5, 1.7, 1.9, 2.7, 2.9, 4.6, 7.1, 7.2, 7.5

Elemental analysis value (%): $C_{23}H_{26}N_2O_4S$

Calculated (%) C, 66.77; H, 6.14; N, 6.57; O, 15.00; S, 7.52.

Found (%) C, 64.37; H, 5.86; N, 6.16; O, 15.82; S, 7.75.

Preparation Example 2

Synthesis of Compound 2

To 150 ml of methanol, 130 g (0.397 mol) of an N-substituted succinimide thio group-containing carboxylic acid and 41.5 ml (0.397 mol) of t-butyl amine were charged and reacted at room temperature for 10 minutes. After the end of the reaction, the methanol was removed under a reduced pressure and the resultant mixture was filtered. The product was washed with acetone twice and dried, then was subjected to the reaction of the following reaction scheme to thereby obtain a white powder compound 2 in an amount of 157 g (yield 99%).

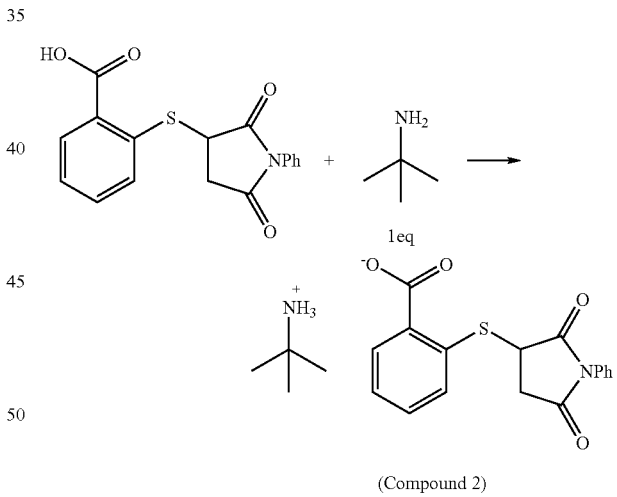

(Compound 2)

$^1$H NMR (400 MHz, DMSO-d6) δ in ppm: 1.0-1.3, 1.5, 2.7, 2.9, 4.6, 7.1, 7.2, 7.5

Elemental analysis value (%): $C_{23}H_{26}N_2O_4S$

Calculated (%) C, 62.98; H, 6.04; N, 6.99; O, 15.98; S, 8.01.

Found (%) C, 62.44; H, 6.07; N, 6.77; O, 16.23; S, 8.14.

Preparation Example 3

Synthesis of Compound 3

In 150 g of methyl ethyl ketone, 15.4 g (0.1 mol) of thiosalicylic acid and 17.3 g (0.1 mol) of N-phenyl maleimide were reacted at 90° C. for 5 hours. After the end of the reaction, the reaction product was concentrated at 90° C. in vacuo to obtain a compound having the following formula in an amount of 32.5 g (yield 99%).

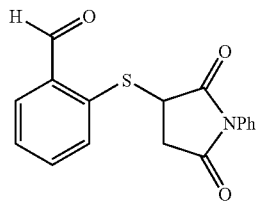

method, the modulus at the time of 100% elongation (M100) were determined and these values were used as the initial values. Furthermore, the other samples of the vulcanization sheets of the unvulcanized rubber compositions were determined according to JIS K 6257 method for the M100 after aging at 100° C. for 96 hours. The results are shown in Table I. Note that the rates of change (%) in the values after aging based on the above initial values were determined according to the following formula:

[(M100 after aging)−(M100 before aging)]×100/ (M100 before aging)

The smaller the value of the rate of change, the more superior the heat aging resistance exhibited.

TABLE I

|  | Comp. Ex. 1 | Comp. Ex. 2 | Ex. 1 | Ex. 2 | Ex. 3 | Ex. 4 | Ex. 5 |
| --- | --- | --- | --- | --- | --- | --- | --- |
| Formulation (parts per weight) | | | | | | | |
| Brominated butyl rubber*1 | 100 | 100 | 100 | 100 | 100 | 100 | 100 |
| Carbon black*2 | 60 | 60 | 60 | 60 | 60 | 60 | 60 |
| Stearic acid*3 | 1 | 1 | — | — | 1 | — | — |
| Oil*4 | 11 | 11 | 11 | 11 | 11 | 11 | 11 |
| Sulfur*5 | 0.53 | — | — | — | 0.53 | — | — |
| Vulcanization accelerator*6 | 1.05 | — | — | — | — | — | — |
| Compound 1 (Preparation Example 1) | — | — | 2 | 2.5 | 2 | — | — |
| Compound 2 (Preparation Example 2) | — | — | — | — | — | 2 | 2 |
| Compound 3 (Preparation Example 3) | — | 2 | — | — | — | — | — |
| Zinc oxide*7 | 2 | — | — | — | — | 2 | — |
| Magnesium oxide*8 | — | 2 | 2 | 2 | — | — | 2 |
| Evaluated Properties | | | | | | | |
| M100 (before aging) | 1 | 1.1 | 1.6 | 1.5 | 1 | 1.8 | 1.3 |
| M100 (after aging) | 1.4 | 1.4 | 1.8 | 1.8 | 1.2 | 1.7 | 1.8 |
| M100 rate of change (%) | 40 | 27 | 13 | 20 | 20 | −5 | 38 |

Footnotes of Table I
*1Brominated butyl rubber manufactured by Bayer Polysar B.N.Y.
*2GPF carbon black manufactured by Mitsubishi Chemical Corporation
*3NOF Corporation
*4Paraffin oil manufactured by Showa Shell Sekiyu K.K.
*5Sulfur fine powder manufactured by Tsurumi Chemical Co., Ltd.
*6Noccelar-DM manufactured by Ouchi Shinko Chemical Industrial Co., Ltd.
*7Seido Chemical Industry Co., Ltd.
*8Kyowa Chemical Industry Co., Ltd.

Examples 1 to 5 and Comparative Examples 1 and 2

Preparation of Sample

In the formulation shown in Table I, the components excluding the vulcanization accelerator and sulfur were mixed in a 1.8 liter Banbury mixer for 5 minutes. The resultant mixture was discharged, when reaching 140° C., to thereby obtain the master batch. Then, the vulcanization accelerator and sulfur were mixed to this master batch by an open roll to obtain the rubber composition.

Then, the unvulcanized rubber composition obtained above was vulcanized in a 15×15×0.2 cm mold at 148° C. for 30 minutes (or at 180° C. for 10 minutes) to prepare a vulcanized rubber sheet, then the following test method was used to determine the tensile characteristics of the vulcanized rubber. The results are shown in Table I.

Evaluation Test Method for Physical Properties of Rubber (Tensile Characteristics)

JIS No. 3 dumbbell test pieces were punched out from these vulcanized sheets. Then, according to JIS K6251

From the above results, it is clear that the novel vulcanization agent/vulcanization accelerator according to the present invention has a high vulcanization efficiency and superior heat aging resistance compared to existing vulcanization systems.

INDUSTRIAL APPLICABILITY

As explained above, it is verified that the novel amine salt compound of a carboxylic acid according to the present invention, when compounded into a rubber composition, provides a high vulcanization efficiency and superior heat aging resistance compared to conventional compounding agents. Furthermore, a performance equal to or greater than a rubber composition of a zinc oxide formulation is shown even without adding zinc oxide. Furthermore, it is possible to use a compounding agent in a zinc oxide-free formulation according to the present invention and which is environmentally friendly.

The invention claimed is:

1. An amine salt compound of a carboxylic acid containing a thermal dissociation portion, represented by the Formula (I):

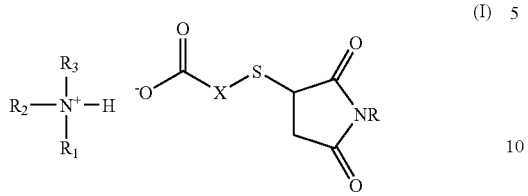

(I)

wherein R represents a group selected from the group consisting of $C_1$ to $C_{20}$ alkyl groups, $C_3$ to $C_{10}$ cycloalkyl groups, $C_6$ to $C_{20}$ aryl groups and $C_7$ to $C_{30}$ alkaryl groups, $R_1$, $R_2$ and $R_3$ independently represent that the two of which are, a hydrogen atom and the other of which represents a $C_1$ to $C_{20}$ alkyl group, cycloalkyl group, aryl group or alkaryl group, all of which may have a substituent group and X represents a $C_6$ to $C_{20}$ arylene group which may have a substituent group.

2. A method for producing an amine salt compound of a carboxylic acid containing a thermal dissociation portion represented by the Formula (I) according to claim 1 comprising the step of reacting a carboxylic acid (II) and an amine (III) under the following reaction scheme:

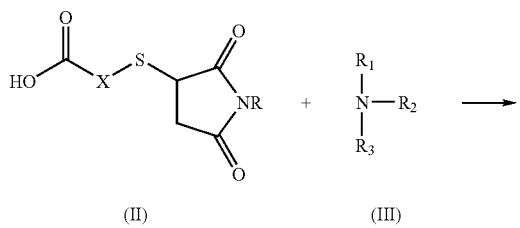

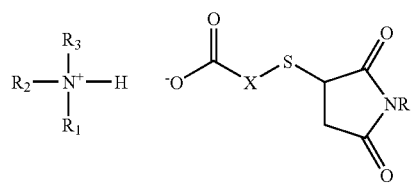

(I)

wherein R, $R_1$, $R_2$ and $R_3$ and X are the same as defined in claim 1.

3. A compounding agent for rubber vulcanization comprised of an amine salt compound of a carboxylic acid containing a thermal dissociation portion, represented by Formula (I) according to claim 1.

4. A rubber composition comprising of 100 parts by weight of an unvulcanized rubber component selected from the group consisting of diene-based rubbers and halogenated rubbers and 0.5 to 10 parts by weight of an amine salt compound of a carboxylic acid containing a thermal dissociation portion, represented by Formula (I) according to claim 1.

* * * * *